(12) United States Patent
Margheritis

(10) Patent No.: US 8,336,739 B2
(45) Date of Patent: Dec. 25, 2012

(54) FLUID DISPENSER DEVICE

(75) Inventor: Antonio Margheritis, Cittiglio (IT)

(73) Assignee: Aptar France SAS, Le Neubourg (FR)

( * ) Notice: Subject to any disclaimer, the term of this patent is extended or adjusted under 35 U.S.C. 154(b) by 257 days.

(21) Appl. No.: 12/446,056

(22) PCT Filed: Oct. 15, 2007

(86) PCT No.: PCT/FR2007/052153
§ 371 (c)(1),
(2), (4) Date: Apr. 17, 2009

(87) PCT Pub. No.: WO2008/047035
PCT Pub. Date: Apr. 24, 2008

(65) Prior Publication Data
US 2010/0237102 A1 Sep. 23, 2010

(30) Foreign Application Priority Data
Oct. 20, 2006 (FR) ...................................... 06 54402

(51) Int. Cl.
*B67B 1/00* (2006.01)
*G01F 11/00* (2006.01)
(52) U.S. Cl. ......... 222/153.07; 222/153.06; 222/153.13; 222/321.8
(58) Field of Classification Search ............. 222/153.01, 222/153.05–153.07, 153.13, 153.14, 321.6–321.8, 222/340, 541.1, 541.6; 239/333, 337
See application file for complete search history.

(56) References Cited

U.S. PATENT DOCUMENTS

| 3,180,532 | A | * | 4/1965 | Michel | 222/182 |
| 4,962,864 | A | * | 10/1990 | Appal et al. | 220/270 |
| 5,722,568 | A | * | 3/1998 | Smith | 222/153.06 |
| 6,257,454 | B1 | * | 7/2001 | Ritsche | 222/153.13 |
| 2004/0139964 | A1 | | 7/2004 | Langford | |
| 2004/0149756 | A1 | * | 8/2004 | Kaufman et al. | 220/257.1 |

FOREIGN PATENT DOCUMENTS

| EP | 1 108 477 A1 | 6/2001 |
| FR | 1.447.222 A | 6/1966 |
| FR | 2.060.343 A | 6/1971 |

* cited by examiner

Primary Examiner — Darren W Gorman
(74) Attorney, Agent, or Firm — Sughrue Mion, PLLC

(57) ABSTRACT

A fluid dispenser device having a fluid dispenser member, the fluid dispenser member fastened by a fastener ring (30) on a reservoir (1). An actuator head (20) is mounted on the dispenser member and is movable so as to actuate the dispenser member. A removable blocking element (40), in its blocking position, prevents the dispenser member from being actuated. At least one breakable element (50) is secured to the blocking element so as to indicate first use. The blocking element is assembled around the fastener ring (30), between the head (20) and the reservoir (1), and, in its blocking position, co-operates with the actuator head and the reservoir so as to prevent the actuator head from moving axially relative to the reservoir. The breakable element (50) surrounds the blocking element (40), at least in part, before first use.

15 Claims, 3 Drawing Sheets

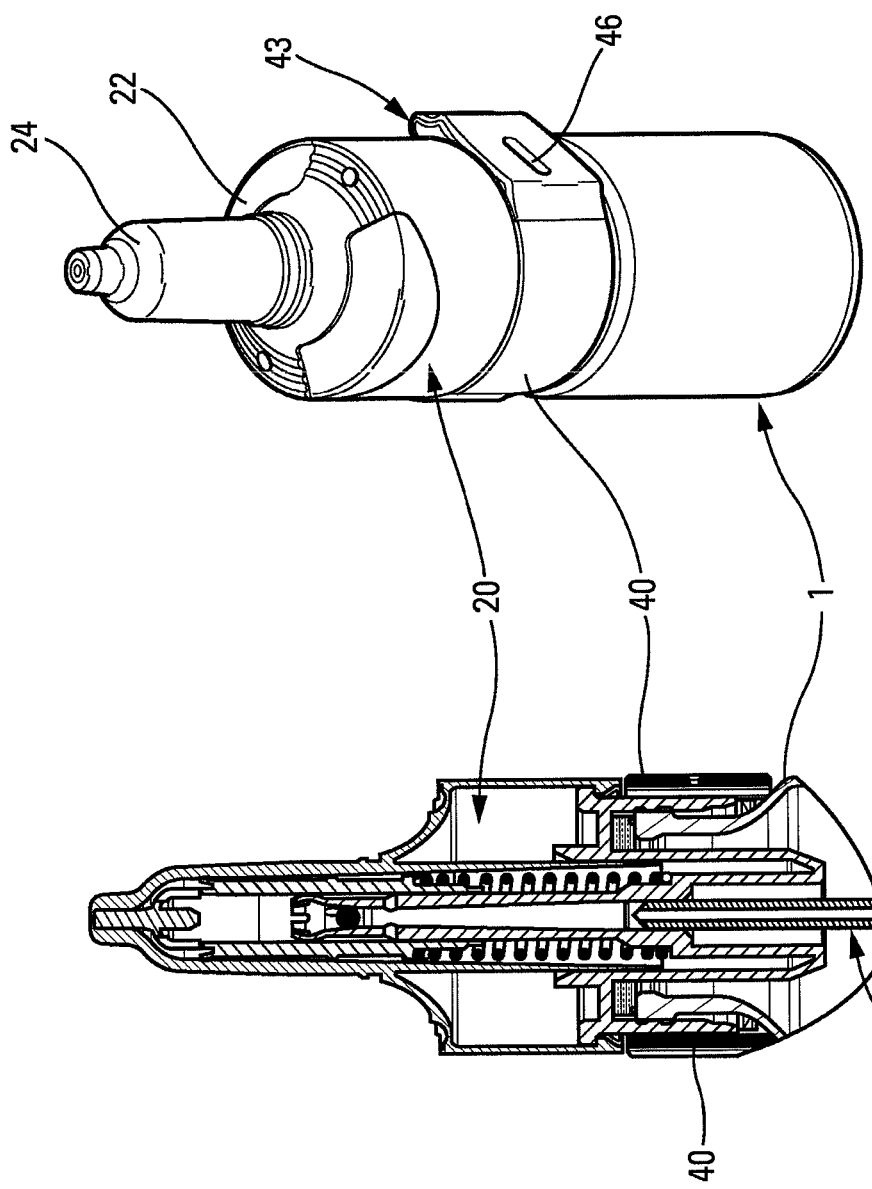
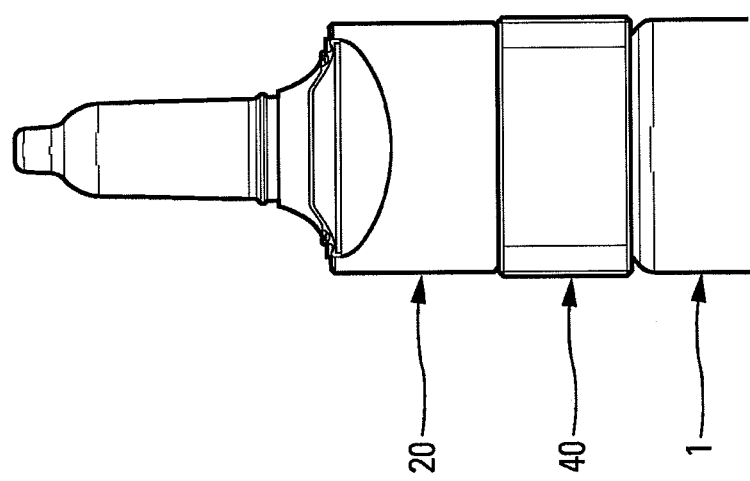

FLUID DISPENSER DEVICE

FIELD OF INVENTION

The present invention relates to a fluid dispenser device and more particularly to such a device including a blocking element making it possible to prevent said device being actuated between two uses.

BACKGROUND

Systems that are used to prevent a fluid dispenser device from being actuated between two actuations are well known and generally include removable devices, such as clips, that are fitted under the actuator head or pusher so as to prevent it from moving. The drawback of such a removable device is that is can sometimes become detached on its own, e.g. while being carried in a bag. Systems exist that are integrated in the device and that are not removable, but such systems are generally very complicated to make and to assemble, and require several parts of the dispenser device to be modified, thereby considerably increasing cost.

SUMMARY OF CERTAIN OBJECTS OF THE INVENTION

An object of the present invention is to provide a fluid dispenser device that does not have the above-mentioned drawbacks.

More particularly, an object of the present invention is to provide a fluid dispenser device including an actuation-blocking element that is simple and inexpensive to manufacture and to assemble.

Another object of the present invention is to provide such a fluid dispenser device that can be adapted easily to existing devices and that does not require modification of the component parts of the dispenser device.

Another object of the present invention is to provide such a device that makes it easy to see whether or not the device has already been used.

Another object of the present invention is to provide such a device that is safe and reliable to operate and that is easy for the user to actuate.

The present invention thus provides a fluid dispenser device, comprising a fluid dispenser member such as a manually-actuated pump or valve, said fluid dispenser member being fastened by a fastener ring on a reservoir; an actuator head that is mounted on said dispenser member, and that is movable so as to actuate said dispenser member; a removable blocking element that, in its blocking position, prevents the dispenser member from being actuated; and at least one breakable element that is secured to the blocking element so as to indicate first use; said blocking element being assembled around the fastener ring, between the head and the reservoir, and, in its blocking position, co-operating with said actuator head and said reservoir so as to prevent said actuator head from moving axially relative to said reservoir, said at least one breakable element surrounding said blocking element, at least in part, before first use.

Advantageously, said breakable element is clipped on said blocking element while it is being assembled.

Advantageously, said blocking element includes at least one opening that is adapted to receive at least one clip element for clipping said breakable element.

Advantageously, the blocking element includes at least one projection that extends radially towards the inside of said blocking element.

Advantageously, the blocking element comprises an open ring that is elastically deformable.

Advantageously, the blocking element (40) and said at least one breakable element (50) form a closed ring before first use.

Advantageously, said at least one breakable element is adapted to break when it is separated from the blocking element.

Advantageously, said at least one breakable element is formed by a strip that interconnects the two sides of said open ring before first use.

Advantageously, before first use, said strip: at a first end, has a solid connection to a first of said two sides of said open ring; extends around the portion of the side wall of said fastener ring that is not encircled by said open ring; and, at a second end, co-operates with the second of said two sides of said open ring.

Advantageously, said strip breaks at the solid connection between said strip and said open ring.

Advantageously, the blocking element is held in its blocking position by retaining means, said retaining means being elastically deformable.

Advantageously, said retaining means are formed by said open ring and/or by at least one blocking projection.

Advantageously, said blocking element includes grip means for snap-fastening and unfastening said open ring.

BRIEF DESCRIPTION OF THE DRAWINGS

Other characteristics and advantages appear from the following detailed description of an advantageous embodiment of the present invention, given by way of non-limiting example, and with reference to the accompanying drawings, in which:

FIG. 7 is a diagrammatic side view of the fluid dispenser device, in its blocked position.

FIG. 8 is a diagrammatic section view of FIG. 7.

FIG. 9 is a diagrammatic perspective view of the dispenser device in its blocked position, showing the clip opening of the blocking element, the breakable element having already been unclipped.

DETAILED DESCRIPTION OF EXEMPLARY EMBODIMENTS OF THE INVENTION

Figures 1A, 2A:
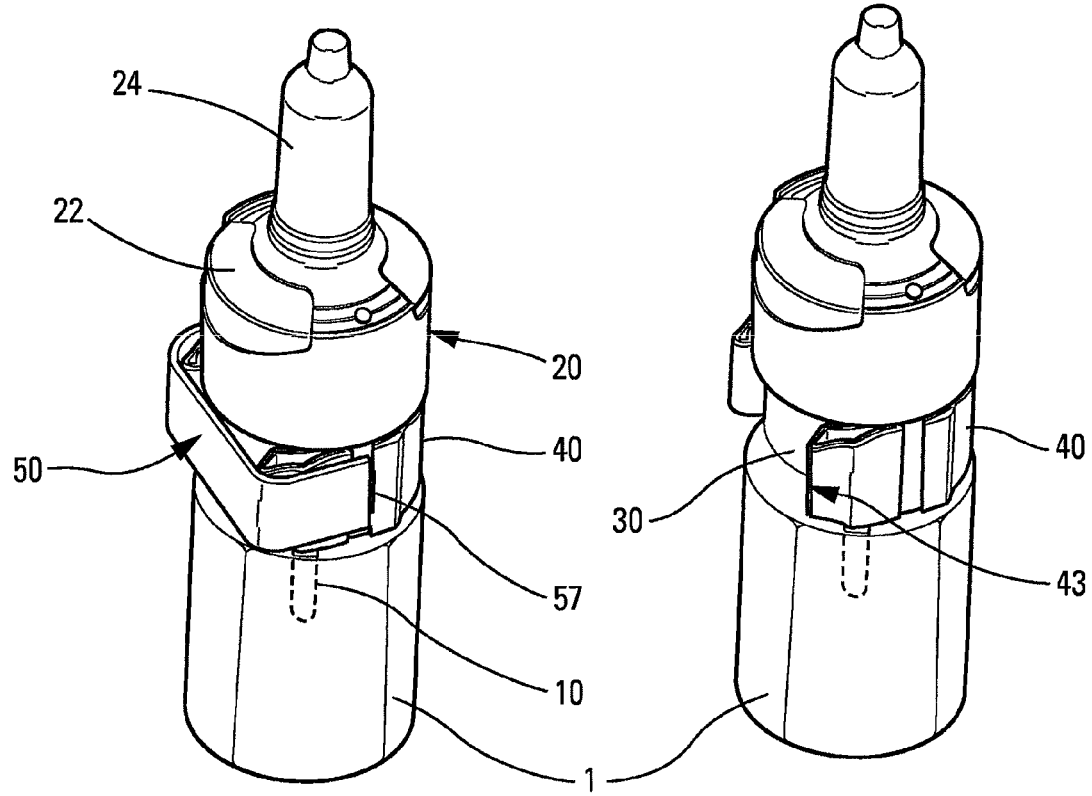
FIGS. 1*a* and 2*a* are diagrammatic perspective views respectively showing a fluid dispenser device in its blocked position before first use, and in its blocked position after first use.
Figures 1B, 2B:
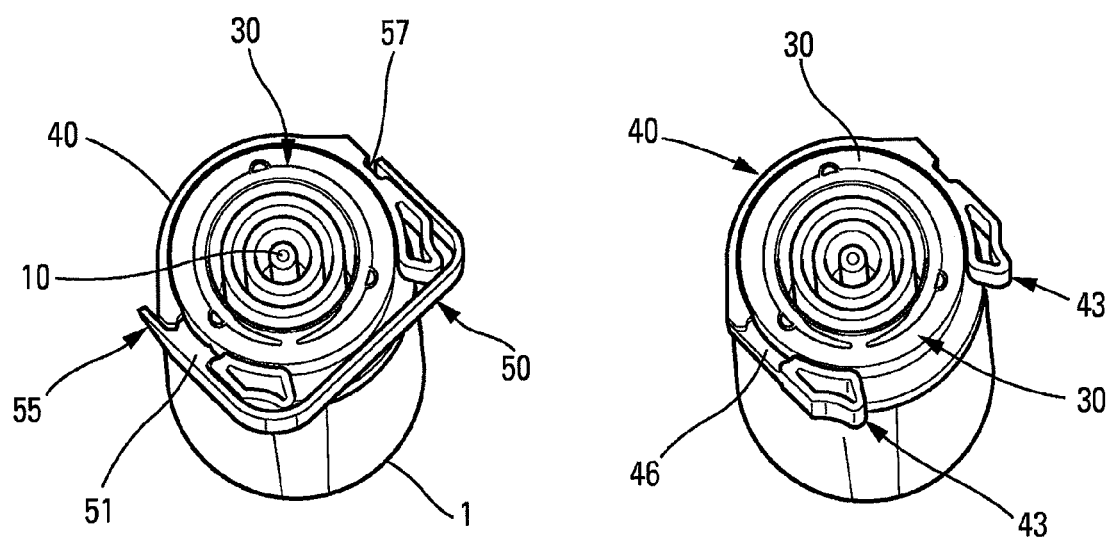
FIGS. 1*b* and 2*b* are diagrammatic horizontal section views showing FIGS. 1*a* and 2*a* respectively.

With reference to the figures, the dispenser device includes a dispenser member 10 that, in the embodiment shown in the figures, is a pump. Naturally, the invention applies to any type of dispenser member, and in particular to valves. The pump can be assembled on a reservoir 1 by means of a fastener ring 30 that can be of any type, and in particular screw fastenable, crimpable, or snap-fastenable. The ring 30 can be a separate element, or it can be made integrally with a portion of the device, such as a piston of the pump, as shown in FIG. 8. The pump body could also be made integrally with the reservoir, in which event the one-piece connection part between the pump body and the reservoir could act as a fastener ring in the meaning of the present invention. A pusher or actuator head 20 is assembled on the pump so as to actuate the pump. In the embodiment shown in the figures, the actuator head is a nasal pusher that includes a longitudinal portion 24 for penetrating into the nostril, and a bearing zone 22 on which the user presses so as to actuate the device. Naturally, the embodiment shown in the figures, in particular the type of pump or the type of pusher, is absolutely not limiting, and, on the contrary, the present invention can apply to any type of fluid dispenser device.

In the invention, the device includes an actuation-blocking element 40 that is assembled on the device in removable manner between a blocking position in which it prevents the pump from being actuated, and a withdrawn position in which the blocking element 40 is removed from the dispenser device, thereby enabling the pump to be actuated. In its blocking position, the blocking element 40 is assembled around the fastener ring 30 between the actuator head 20 and the reservoir 1, as shown in the figures. This embodiment is not limiting, and the ring could also co-operate with another element, that would in turn advantageously co-operate with the blocking element 40. In its blocking position, the purpose of the blocking element is to prevent the head from moving relative to the pump, thereby preventing said pump from being actuated. Advantageously, the blocking element is movable transversally relative to the longitudinal axis of the dispenser member 10, as shown in the figures. At least one grip means 43 for gripping the blocking element make it easy for the user to put the blocking element into place around the fastener ring, and/or to remove it therefrom. The grip means can consist of edges that are thicker compared to the structure of the blocking element. As shown in the figures, the grip means could be an edge having double side walls that project beyond the blocking element, and thus can be accessed easily by the user.

The blocking element includes first-use indicator means comprising at least one breakable element 50. The figures show an embodiment with a single breakable element, but a plurality could be provided. In the blocking position before first use, the breakable element surrounds the blocking element, at least in part. During first use, the breakable element is adapted to break and to become separated from the blocking element.

Figure 3:
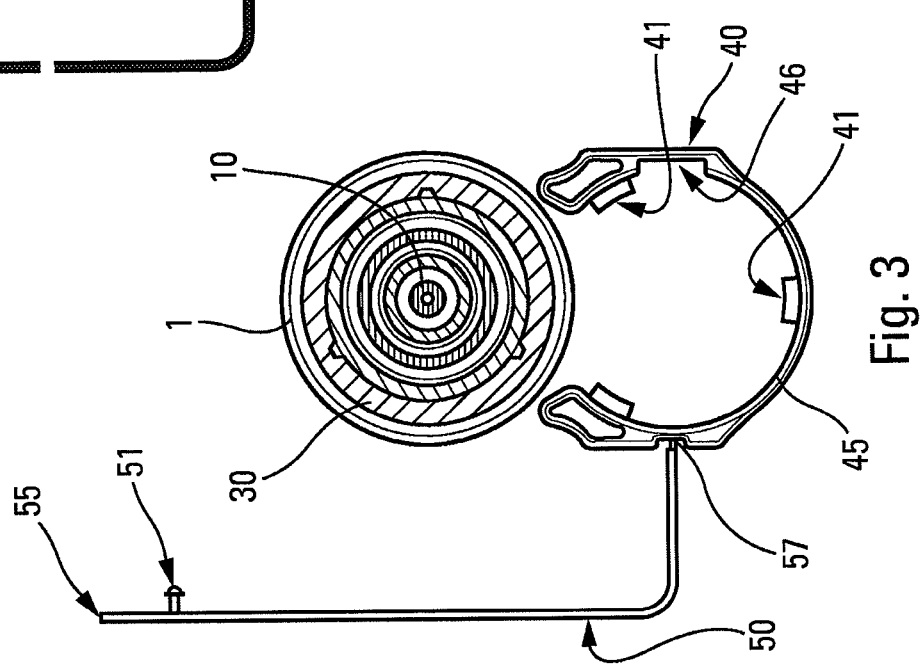
FIG. 3 is a horizontal section view of the device, before the blocking element is assembled to the fastener ring.

As shown in FIG. 3, the blocking element can include at least one projection 41. Said at least one projection extends radially inwards from the inside wall of the blocking element. Thus, when the blocking element 40 is in its blocking position around the fastener ring 30, said at least one projection can be inserted between the bottom edge of the fastener ring 30 and the reservoir 1. Said projection can thus serve to wedge the blocking element around the fastener ring, and thereby avoid any movement of the blocking element when it is in its blocking position. Said at least one projection 41 can also co-operate with other component parts of the device.

In the embodiment shown in the figures, the blocking element advantageously includes an open ring 45 that is elastically deformable. FIG. 3 shows the open ring before it is mounted on the fastener ring 30. The open ring can include three projections 41 that are disposed symmetrically about the longitudinal axis of the device, for example. Each of the free ends of the open ring is provided with grip means 43 in the form of a double side wall of substantially rounded shape that comes to snap-fasten easily around the fastener ring. The grip means could also be provided at another location, e.g. in the middle of the open ring. On one side, the side wall of the open ring 45 has a solid connection 57 with the breakable element 50, (before the device is used for the first time), and on its other side, the side wall of the open ring has at least one opening 46 for receiving the clip element 51 for clipping the breakable element.

The blocking element can thus include retaining means that serve to hold the open ring around the fastener ring. The retaining means are elastically deformable so as to enable the open ring to be snap-fastened around the fastener ring and unfastened therefrom. Said retaining means can be provided by the elasticity of the open ring 45 itself, or they can be projections 41. The retaining means are particularly useful once the breakable element has been unclipped from the blocking element, so as to retain said blocking element in its blocking position between separate uses of the dispenser device.

Figure 4:
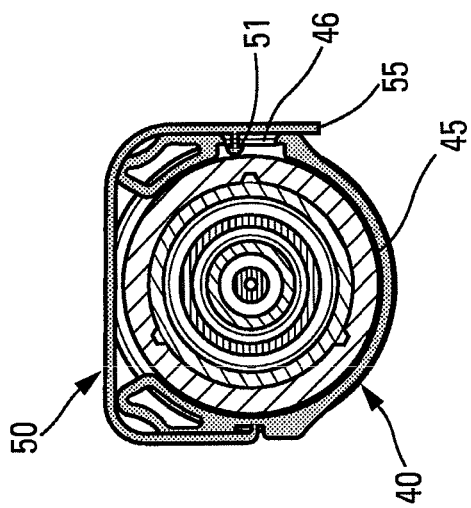
FIG. 4 is a view similar to FIG. 3, after the blocking element has been assembled to the fastener ring.
Figure 5:
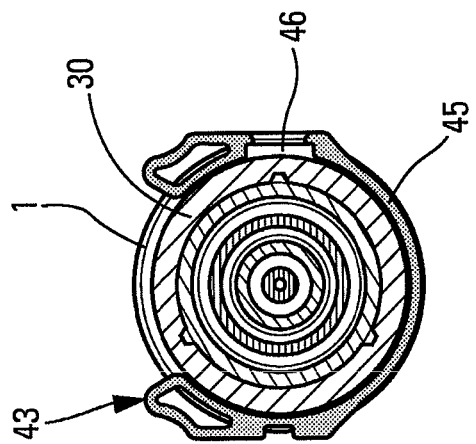
FIG. 5 is a view similar to FIG. 4, showing the dispenser device after the breakable element has been clipped on the blocking element.
Figure 6:
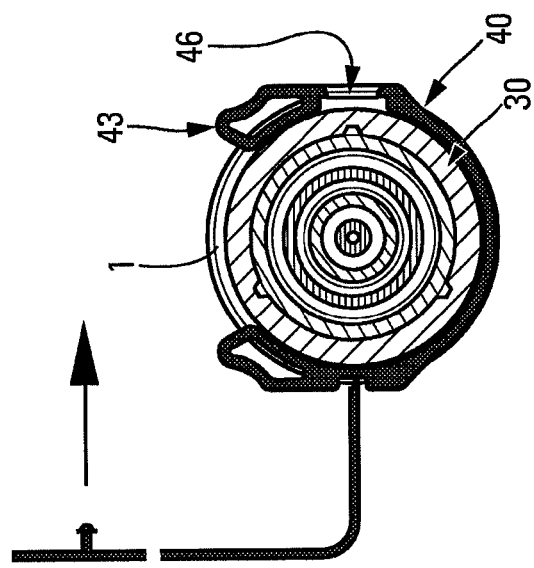
FIG. 6 is a view similar to FIG. 5, in the blocked position, after the breakable element has been separated from the blocking element after first use.

The breakable element is secured to the blocking element by the solid connection piece 57 situated on the outside wall of the open ring, as shown in FIGS. 3 to 5. The breakable element extends around the fastener ring at least in part, with its free end 54 meeting the side wall on the other side of the open ring. The free end of the breakable element 50 includes a clip element 51, e.g. a pin head or the like, that comes into engagement in a corresponding opening 46 situated on said other side of the open ring.

Thus, after the initial assembly of the blocking element 40 and of the clip-carrying breakable element 50 around the fastener ring 30, the dispenser device is blocked in its blocked position by a closed ring, said closed ring being constituted by the open ring 45 having ends that are interconnected by means of the breakable element 50. The breakable element can be made of a material that is flexible enough to be fitted and positioned firstly tightly against the edges 43 of the open ring, and secondly tightly against the portion of the side wall of the fastener ring that is not encircled by said open ring. Only the edge 55 of the clip-carrying free end projects a little beyond the closed ring system, thereby constituting unclipping means 55 that can be accessed easily by the user and that make it easy to unclip and separate the breakable element on first use.

The blocking element, including the breakable element, is advantageously made of plastics material that is both strong, so as to enable the blocking element to be reusable, and deformable, so as to enable the blocking element to be snap-fastened and unfastened, and so as to enable the breakable element to be adapted during assembly to the shape of the blocking element and of the fastener ring.

In an advantageous embodiment, the breakable element forms a strip that extends on one side of the open ring, then along the side wall of said side of the open ring towards the edge of the ring, then extends around the portion of the side wall of said fastener ring that is not encircled by the open ring, then meets the edge of the other side of the open ring, the free end of said strip thus clipping into the opening in said same side, while continuing its path around the open ring so as to allow its free edge, that constitutes the unclipping means 55, to project therebeyond.

During first use, unclipping the breakable element 50 causes it to be separated, preferably automatically, from the open ring 40 at its solid connection 57 with said open ring. It then remains for the user to unfasten the blocking element 40 from the fastener ring 30 so as to put the dispenser device into its dispensing position and enable the pump to be actuated. The presence of a strip 50 that is clipped on the blocking element and that is still intact thus guarantees to the user that the blocking element 40 has not yet been removed from its blocking position. Thus, it is certain that the device has never been actuated.

After first use, the ring can be put back into place in its blocking position. It suffices for the user to snap-fasten the open ring around the fastener ring. Snap-fastening is facilitated by the shape of the edges of the two ends of the open ring at the grip means 43. As shown in FIG. 3, each of the two edges of the grip means, when put into contact with the fastener ring, is tangential to the circular wall of the fastener ring, so as to make it easier for the ends of the ring to slide around the head until they become snap-fastened. The shape of the edges of the ends of the ring presents the other advantage of not damaging the actuator head during successive snap-fastenings and unfastenings of each subsequent use of the dispenser device. Once snap-fastened, the open ring 45 thus extends once again around the fastener head 30, at least in part, with each blocking projection 41 co-operating with the fastener ring 30 or with an element secured thereto.

Advantageously, the blocking element 40 of the invention can be engaged on the fastener ring 30 via any side. This embodiment is simple and rapid to assemble since it is not necessary to orientate each fastener ring while assembling the blocking element on the fastener ring. In addition, it is very easy for the user to put the blocking element back into place after each use.

Whatever the embodiment, the blocking element of the present invention can advantageously be applied to any existing fluid dispenser devices, without the need for any other modification to the devices.

The present invention is described above with reference to an advantageous embodiment thereof, but naturally it is not limited to the embodiments shown in the drawings. Modifications could be envisaged by the person skilled in the art, without going beyond the ambit of the present invention, as defined by the accompanying claims.

The invention claimed is:

1. A fluid dispenser device comprising:
    a fluid dispenser member, said fluid dispenser member being fastened by a fastener ring on a reservoir;
    an actuator head that is mounted on said dispenser member, and that is movable so as to actuate said dispenser member;
    a removable blocking element that, in a blocking position, prevents the dispenser member from being actuated; and
    at least one breakable element that is secured to the blocking element so as to indicate first use;
    said blocking element is assembled around the fastener ring, between the head and the reservoir, and, in the blocking position, cooperates with said actuator head and said reservoir so as to prevent said actuator head from moving axially relative to said reservoir, said at least one breakable element surrounding said blocking element, at least in part, before first use; and
    said blocking element is structured to be detached and reattached to the dispenser device so as to be reusable without loss of the blocking element's ability to cooperate with the actuator head and the reservoir so as to prevent the actuator head from moving axially relative to the reservoir; and
    wherein the blocking element is detached and reattached by movement transverse relative to a longitudinal axis of the dispenser member.

2. A device according to claim 1, wherein said breakable element is clipped on said blocking element while being assembled.

3. A device according to claim 2, wherein said blocking element includes at least one opening that is adapted to receive at least one clip element for clipping said breakable element.

4. A device according to claim 1, wherein the blocking element includes at least one projection that extends radially towards the inside of said blocking element.

5. A device according to claim 1, wherein the blocking element comprises an open ring that is elastically deformable.

6. A device according to claim 5, wherein the blocking element and said at least one breakable element form a closed ring before first use.

7. A device according to claim 1, wherein said at least one breakable element is adapted to break when separated from the blocking element.

8. A device according to claim 5, wherein said at least one breakable element is formed by a strip that interconnects the two sides of said open ring before first use.

9. A device according to claim 8, wherein, before first use, said strip:
    at a first end, has a solid connection to a first of said two sides of said open ring;
    extends around the portion of the side wall of said fastener ring that is not encircled by said open ring; and
    at a second end, co-operates with the second of said two sides of said open ring.

10. A device according to claim 8, wherein said strip breaks at a solid connection between said strip and said open ring.

11. A device according to claim 1, wherein the blocking element is held in its blocking position by retaining means, said retaining means being elastically deformable.

12. A device according to claim 11, wherein said retaining means are formed by an open ring and/or by at least one projection.

13. A device according to claim 5, wherein said blocking element includes grip means for snap-fastening and unfastening said open ring.

14. The device according to claim 1, wherein said fluid dispenser is a manually actuated pump or valve.

15. A fluid dispenser device comprising:
    a fluid dispenser member fastened by a fastener ring on a reservoir;
    an actuator head mounted on the dispenser member and movable so as to actuate the dispenser member;
    a blocking element that is removable and when, in a blocking position, prevents the dispenser member from being actuated; and
    a breakable element secured to the blocking element so as to indicate first use;
    the blocking element assembled around the fastener ring between the head and the reservoir, and, in the blocking position, co-operates with the actuator head and the reservoir to prevent the actuator head from moving relative to the reservoir, the breakable element surrounding the blocking element, at least in part, before first use; and
    the blocking element is structured to be detached and reattached to the dispenser device so as to be reusable without loss of the blocking element's ability to co-operate with the actuator head and the reservoir so as to prevent the actuator head from moving axially relative to the reservoir;
    wherein the blocking element is detached and reattached by movement transverse relative to a longitudinal axis of the dispenser member, the actuator head moving along the longitudinal axis of the dispenser member to actuate the dispenser member.

* * * * *